United States Patent
Giddings

(10) Patent No.: US 9,933,383 B2
(45) Date of Patent: Apr. 3, 2018

(54) MOISTURE SENSOR FOR A GRAIN DRYER

(71) Applicant: SUKUP MANUFACTURING CO., Sheffield, IA (US)

(72) Inventor: Graham Giddings, Sheffield, IA (US)

(73) Assignee: Sukup Manufacturing Co., Sheffield, IA (US)

( * ) Notice: Subject to any disclaimer, the term of this patent is extended or adjusted under 35 U.S.C. 154(b) by 53 days.

(21) Appl. No.: 14/736,492

(22) Filed: Jun. 11, 2015

(65) Prior Publication Data

US 2016/0363554 A1  Dec. 15, 2016

(51) Int. Cl.
*G01N 27/22* (2006.01)

(52) U.S. Cl.
CPC .................. *G01N 27/223* (2013.01)

(58) Field of Classification Search
CPC .................................... G01N 27/223
USPC ............................................. 73/73
See application file for complete search history.

(56) References Cited

U.S. PATENT DOCUMENTS

| | | | | |
|---|---|---|---|---|
| 4,003,618 A * | 1/1977 | Booty | ................ | H01R 25/162 439/113 |
| 5,144,755 A | 9/1992 | Braun et al. | | |
| 5,661,227 A * | 8/1997 | Smith | ................ | G01N 27/048 324/694 |
| 6,101,742 A * | 8/2000 | Middaugh | ............ | F26B 25/002 34/166 |
| 8,033,847 B1 * | 10/2011 | Chen | .................... | H01R 13/652 439/172 |
| 8,479,408 B2 | 7/2013 | Salisbury | | |
| 8,806,772 B1 | 8/2014 | Schaefer, Jr. | | |
| 2011/0110792 A1 * | 5/2011 | Mauro | .................... | F04B 49/02 417/44.1 |
| 2013/0255783 A1 * | 10/2013 | Runge | ................ | A01G 25/167 137/1 |

OTHER PUBLICATIONS

Dryer Master, Inc., "Real-Time Moisture Measurement" http://dryermastercom/technology (retrieved from Internet on Feb. 23, 2015), 3 pages.

Sukup Manufacturing Company, "Sukup Grain Dryers", Brochure L1130-012015P, dated Jan. 2015, 12 pages.

* cited by examiner

*Primary Examiner* — Hezron E Williams
*Assistant Examiner* — Tarun Sinha
(74) *Attorney, Agent, or Firm* — Zarley Law Firm, P.L.C.

(57) ABSTRACT

A moisture sensor for drying grain having a sensor block with built in ground bars, a removable electronic module having a circuit board encased in black potting compound, and a removable back plate.

15 Claims, 4 Drawing Sheets

MOISTURE SENSOR FOR A GRAIN DRYER

BACKGROUND OF THE INVENTION

The present invention is directed to a moisture sensor and more particularly a moisture sensor for use in drying grain.

Moisture sensors are known in the art and are used in part to measure the moisture of grain as it enters, and more typically, leaves a grain dryer. Use of a moisture sensor with a grain dryer is important as it permits automatic adjustments that cause the dryer to run faster or slower to obtain a desired moisture content of the grain.

While valuable, there remain issues with present moisture sensors. As an example, to protect a circuit board, a two-part gel is heated at a high temperature in order to set up. The high temperature places stress on electronic components making the electronics less dependable and more susceptible to failure. Plus, the circuit board's performance can be affected by heat transfer from high grain temperatures. Also, present moisture sensors have limited accuracy typically operating at 2 MHz and are grounded to a tube of steel. Finally, if a component in the moisture sensor fails the entire sensor must be discarded. Accordingly, there exists a need in the art for a moisture sensor that addresses these deficiencies.

Therefore, an objective of the present invention is to provide a moisture sensor that is more dependable.

Another objective of the present invention is to provide a moisture sensor with improved performance and accuracy.

A still further objective of the present invention is to provide a moisture sensor where components can be replaced without replacing the entire moisture sensor.

These and other objectives will be apparent to one skilled in the art based upon the following written description, drawings, and claims.

SUMMARY OF THE INVENTION

A moisture sensor assembly having a sensor block with a cavity formed to receive an electronic module. A wear plate is connected to a top of the sensor block and a back plate is connected to a bottom surface of the sensor block. Both a moisture sensor flag and a temperature sensor are connected to the electronic module and extend through and away from the sensor block and the wear plate. A cable connector is connected to the electronic module and extends through and away from the back plate. The wear plate has a pair of grooves that receive grounding bars that are connected to the back plate and the electronic module.

DETAILED DESCRIPTION OF THE PREFERRED EMBODIMENT

Figure 1:
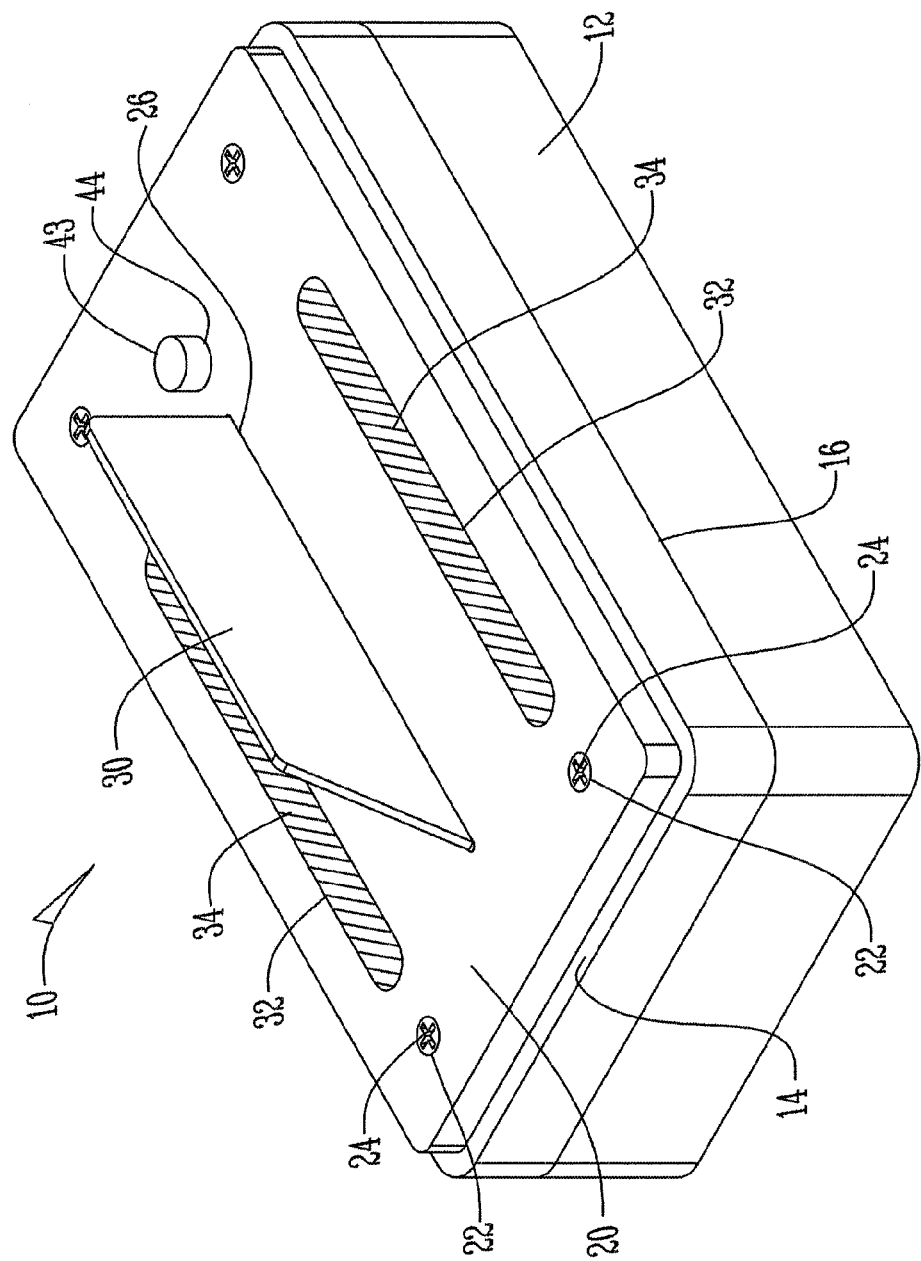
FIG. 1 is a perspective view of a moisture assembly.
Figure 2:
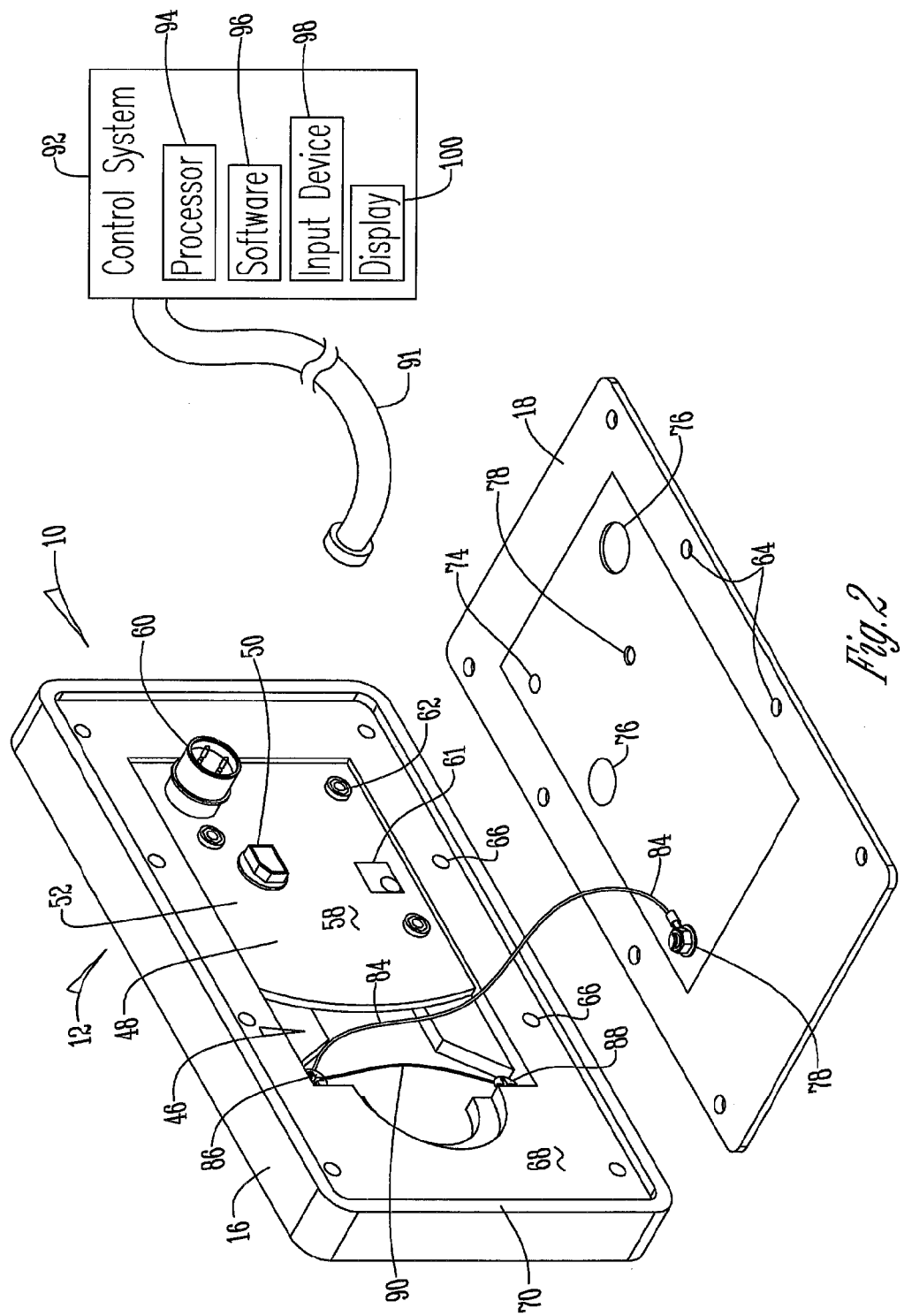
FIG. 2 is a perspective view of a moisture assembly.

Referring to the Figures a moisture sensor assembly 10 has a sensor block 12 having a top 14, sidewalls 16, and a removable back plate 18. Attached to the top 14 of the sensor block 12 is a wear plate 20. The wear plate 20 has a plurality of connection holes 22 that align with threaded holes in the sensor block 12 for receiving bolts 24 to connect wear plate 20 to sensor block 12.

Figure 5:
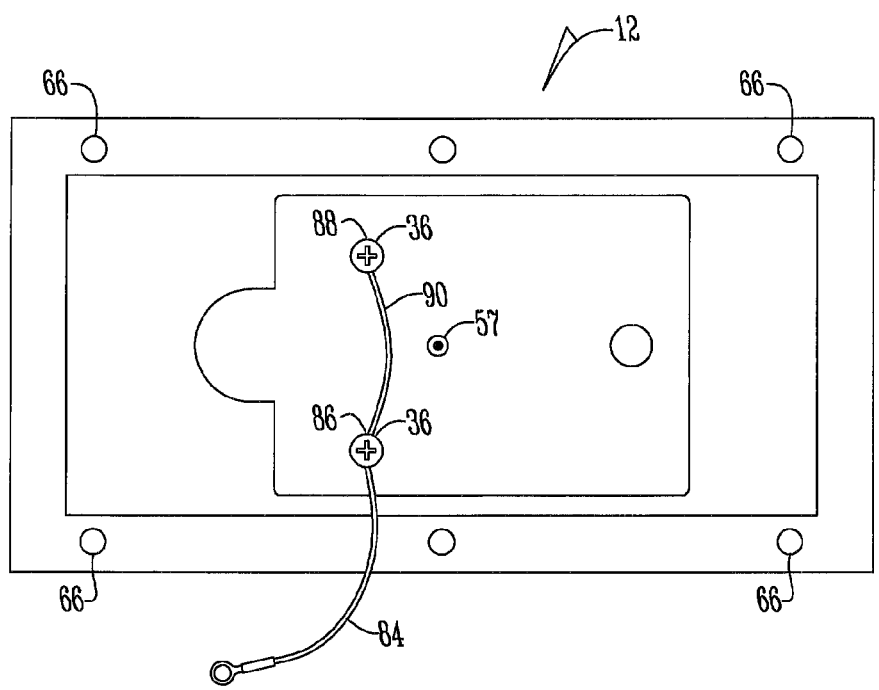
FIG. 5 is a bottom plan view of a sensor block.
Figure 6:
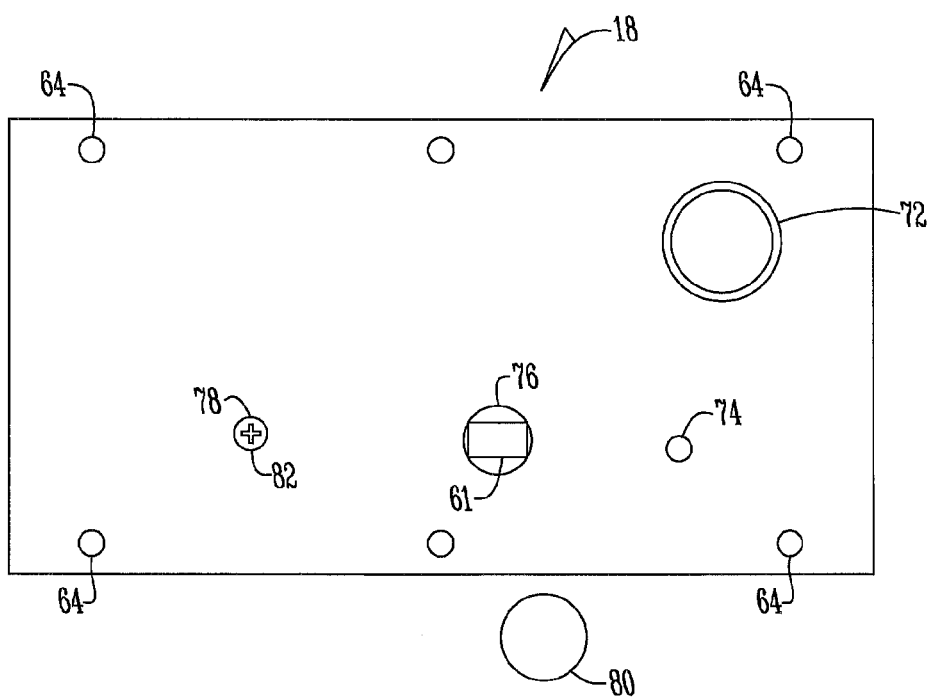
FIG. 6 is a top plan view of a back plate.

An elongated slot 26 extends through the wear plate 20 and the top 14 of the sensor block 12. A moisture flag 30 is received within slot 26 and extends outwardly from wear plate 20. On each side of the moisture flag 30 are a pair of longitudinal grooves 32 formed within the wear plate 20 to receiving grounding bars 34. Each groove 32 has a hole or aperture 36 that extends through the wear plate 20 and the top 14 of the sensor block 12 (See FIG. 5). Another hole or aperture 44 extends through wear plate 20 and the top 14 of the sensor block 12 and is positioned to receive a tube 43 for a temperature/sensor probe 45. The sidewalls 16 and top wall 14 of the sensor block 12 form a cavity 46 opposite the wear plate 20 that is formed to receive an electronic module 48.

Figure 3:
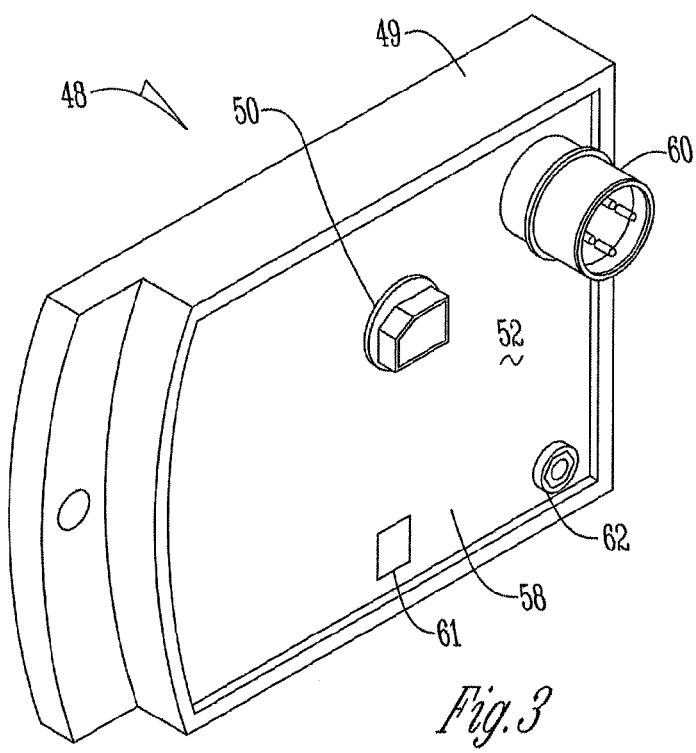
FIG. 3 is a perspective view of an electronic module.
Figure 4:
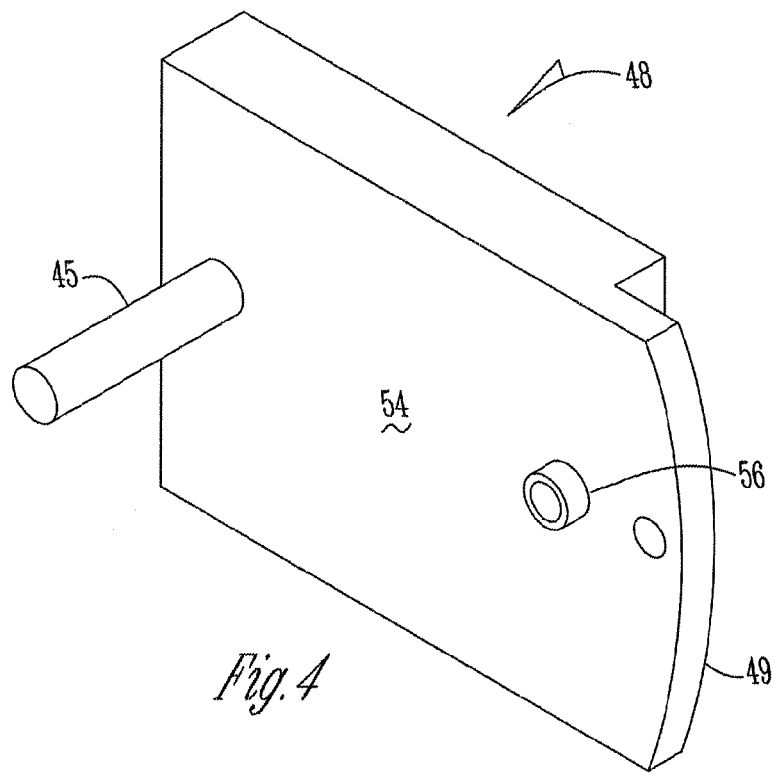
FIG. 4 is a perspective view of an electronic module.

The electronic module 48 as shown in FIGS. 3 and 4 has a tray 49 that receives a circuit board 50 that is encased within a black potting compound 52 that sets up at room temperature. The electronic module 48 has a top or first surface 54. Extending outwardly from top surface 54 is a flag connector 56 that is positioned to receive a pin 57 (See FIG. 5) that is connected to and extends away from the moisture sensor flag 30. The temperature sensor/probe 45 also extends outwardly from the top surface 54 of the electronic module 48 such that sensor 45 extends into tube 43 of sensor block 12. Both the flag connector 56 and the temperature sensor/probe 45 are connected to the circuit board 50.

Extending outwardly from a bottom or second surface 58 of electronic module 48 is a cable connector 60, a potentiometer 61, and a threaded stand off 62. Both the cable connector 60 and the potentiometer 61 are connected to the circuit board 50.

The back plate 18 has a plurality of holes 64 on its outer perimeter that align with bores 66 on a bottom surface of the sensor block 12. Inward from the outer periphery of the back plate 18 is a cable connector hole 72 a grounding hole 74, a potentiometer hole 76, and a ground hole 78. The cable connector hole 72 is positioned to receive the cable connector 60, the connector hole 74 is aligned with the threaded stand off 62, and the potentiometer hole 76 aligns with the potentiometer 61. The potentiometer 61 is used to calibrate/adjust output voltage and plug 80 is inserted into hole 76 to seal hole 76 once the potentiometer 61 is adjusted.

Ground hole 78 receives a screw 82 that serves as a ground for grounding bars 34. A wire 84 is connected to screw 82 at one end and to ground 86 at the opposite end. Ground 86 is connected to ground 88 by wire 90. Both grounds 86 and 88 extend through apertures 36 to engage grounding bars 34.

In operation, the moisture sensor assembly 10 is mounted to an opening in a tube. The sensor assembly 10 is mounted such that the moisture sensor flag 30 and the temperature tube 43 extend into the interior of tube. The moisture sensor flag 30 works as a capacitor whose capacitance varies with changes in moisture content of grain. The circuit board 50 provides an output voltage corresponding to the capacitance of the moisture sensor flag 30. The temperature sensor 45 converts temperature into a voltage representative of the temperature of the grain.

The moisture voltage is transmitted from the electrical module 48 through a cable 91 attached to the cable connector 60. The cable 90 is also connected to a control system 92 having a processor 94, software 96, an input device 98, and a display 100. The control system 92 is connected to and controls the rotational speed of the dryer's unload system at the bottom of grain pathways. The cable is capable of a quick disconnect between control system 92 and module 48. An operator inputs a desired moisture content through the input device 98. The software 96 of the processor 94 compares the desired moisture content with the detected moisture content and sends a signal to the dryer's unload system adjusting the speed of the unload system so that the dryer will operate faster or slower to achieve actual grain moisture at or near the desired moisture content.

What is claimed is:

1. A moisture sensor assembly, comprising:
a sensor block having a cavity formed therein;
a removable electronic module formed to be received within the cavity;
a moisture sensor flag that is connected to the electronic module and extends through and away from the sensor block;
a wear plate having a pair of longitudinal grooves that receive the pair of grounding bars positioned horizontally along a top surface of the wear plate;
a control system connected to the electronic module; and
the pair of grounding bars received within grooves and positioned on either side of the moisture flag along a top surface of the sensor block.

2. The assembly of claim 1 further comprising a back plate connected to the sensor block and the electronic module.

3. The assembly of claim 1 further comprising a wear plate connected to the sensor block.

4. The assembly of claim 1 wherein the ground bars are connected to a ground on a back plate that is connected to the sensor block.

5. The assembly of claim 1 further comprising a temperature sensor connected to the electronic module that extends through and away from the sensor block.

6. The assembly of claim 1 wherein the electronic module has a circuit board that is encased in a black potting compound.

7. The assembly of claim 2 wherein the electronic module has a cable connector that extends through and away from the back plate and a quick disconnect cable attached to the cable connector.

8. The system of claim 1 wherein the connection of the control system to the electronic module is capable of a quick disconnect.

9. A moisture sensor assembly, comprising:
a sensor block having a cavity formed therein;
a wear plate attached to a top of the sensor block;
a pair of grounding bars received within longitudinal grooves positioned horizontally along a top surface of the wear plate;
a moisture flag extending through the top of the sensor block and the wear plate;
an electronic module disposed within the cavity and connected to the moisture flag;
a back plate connected to the sensor block and the grounding bars; and
the pair of grounding bars received within grooves and positioned on either side of the moisture flag along a top surface of the sensor block.

10. A moisture sensor assembly comprising:
a sensor block with a cavity formed therein;
a moisture flag extending through a top of the sensor block;
a pair of grounding bars received within grooves and positioned on either side of the moisture flag along a top surface of the sensor block;
wherein the pair of grounding bars do not extend outwardly and away from the sensor block; and
a removable electronic module connected to the moisture flag wherein the electronic module include a circuit board encased within a black potting compound within a tray.

11. The moisture sensor assembly of claim 9 wherein the grooves have apertures extending through the wear plate and the top of the sensor block.

12. The moisture sensor assembly of claim 10 further comprising a flag connector that is positioned to receive a pin that is connected to and extends away from the moisture sensor flag.

13. The moisture sensor assembly of claim 10 wherein the flag connector is connected to the circuit board.

14. The moisture sensor assembly of claim 1 wherein the controller is configured to control a rotational speed of a grain dryer unload system.

15. The moisture sensor assembly of claim 12 wherein the flag connector extends outwardly from a top surface of the electronic module.

* * * * *